United States Patent
McKinney

(10) Patent No.: US 8,282,686 B2
(45) Date of Patent: Oct. 9, 2012

(54) PROSTHETIC SOCKET

(75) Inventor: Donald Ray McKinney, Gurnee, IL (US)

(73) Assignee: Lincolnshire Manufacturing LLC, Gurnee, IL (US)

( * ) Notice: Subject to any disclaimer, the term of this patent is extended or adjusted under 35 U.S.C. 154(b) by 330 days.

(21) Appl. No.: 12/586,235

(22) Filed: Sep. 18, 2009

(65) Prior Publication Data

US 2011/0071648 A1    Mar. 24, 2011

(51) Int. Cl.
*A61F 2/80* (2006.01)
(52) U.S. Cl. .......................................... 623/34; 623/36
(58) Field of Classification Search .................... 623/34, 623/36, 37
See application file for complete search history.

(56) References Cited

U.S. PATENT DOCUMENTS

| | | | |
|---|---|---|---|
| 6,063,125 A * | 5/2000 | Arbogast et al. | 623/34 |
| 6,267,787 B1 * | 7/2001 | Capper et al. | 623/36 |
| 2008/0221706 A1 * | 9/2008 | Scussel et al. | 623/32 |

* cited by examiner

*Primary Examiner* — David H. Willse
(74) *Attorney, Agent, or Firm* — Bishop & Diehl, Ltd.

(57) ABSTRACT

A socket assembly for use with a prosthetic device. The socket assembly receives at least a portion of a residual limb on which the prosthetic device is attached. The socket assembly includes an airtight outer shell adapted and constructed to receive a portion of the residual limb of an amputee, the shell having an interior and an exterior. A vacuum-permeable skin interface is secured to at least a portion of the interior of the outer shell. A high-vacuum valve communicates between the interior of the socket and the exterior of the socket, the valve being adapted and constructed to be attached to a vacuum source. When the residual limb is positioned in the socket assembly and the high-vacuum valve is connected to a vacuum source, the vacuum force exerted by the source is evenly distributed to the residual limb through the skin interface.

17 Claims, 2 Drawing Sheets

PROSTHETIC SOCKET

CROSS-REFERENCE TO RELATED APPLICATIONS

This application incorporates herein by reference U.S. patent application Ser. No. 11/640,150 filed on Dec. 14, 2006, U.S. patent application Ser. No. 12/286,474 filed Sep. 30, 2008, and U.S. Provisional Application No. 61/192,386 filed Sep. 18, 2008.

TECHNICAL FIELD OF THE INVENTION

The present device relates to a socket assembly for a prosthetic device. In particular, the present device relates to a socket assembly having an outer shell and a skin interface, an air barb communicating with the interior of the socket for connection to a vacuum source.

BACKGROUND OF THE INVENTION

The history of artificial limbs begins with very remote times. There is some evidence that the Romans and the Greeks improvised some sort of substitute for the limbs lost in battle and the vicissitudes of life. Herodotus tells us of a prisoner who amputated his own foot in order to free himself from the shackle, after which he escaped and returned to his friends, who made a wooden foot.

The treasure trove that turned up at Capua in 1885 in a tufa tomb is probably the most valuable and indisputable evidence that artificial legs were made in early times. The relic is now on exhibition in the Museum of the Royal College of Surgeons, London. The official catalogue describes it thus: "Roman artificial leg; the artificial limb accurately represents the form of the leg. It is made with pieces of thin bronze, fastened by bronze nails to a wooden core. Two iron bars, having holes at their free ends, are attached to the upper extremity of the bronze. A quadrilateral piece of iron, found near the position of the foot, is thought to have given strength to it. There was no trace of the foot, and the wooden core had nearly crumbled away."

From those early times to about the beginning of the 20th century, little or no advance was made in the art; and, as no evidence exists to prove to the contrary, it is quite reasonable to suppose that for many centuries the manufacture of artificial limbs was one of the lost arts.

In the early' part of the 20th century, the Duke of Anglesea, being in need of an artificial leg, and possessing an inventive faculty, suggested to an English instrument maker, what proved to be a very answerable substitute, a decided improvement on the primitive peg of the doughty Peter. The leg received but little improvement until the venturesome Selpho introduced it into this country with some admirable modifications of his own; here it met with American enterprise and began to thrive.

Typically, artificial limbs are held in place by a series of straps or some type of suspension system. Some are suspended with a silicone sleeve that has a pin that locks in place.

The earliest use of a vacuum to attach an artificial leg was with above the knee amputees using what is known as the suction socket. This uses the same principle as a suction cup where the maximum strength of the force holding the objects together is a function of the atmospheric pressure at the altitude of use. In artificial leg usage the suction or vacuum is reduced by the vapor pressure of the sweat at the internal temperature of the socket. Use of suction sockets on below knee amputees were not initially practical. The next advance in using vacuum was the introduction of the Harmony system which uses a mechanical pump operated by the energy of walking. Each step operates the pump.

A vacuum system improves the fit and comfort between the device and the residual limb. A vacuum pump forces out air through a one-way valve, creating negative pressure with every step the patient takes. A tiny tube connects the pump to a weight-bearing socket which is enveloped in a urethane liner or sleeve. By improving suspension, the prosthesis offers better control and less pressure on the limb and liner. The pump is powered by the wearer's body weight. Taking a step compresses the device, which creates the vacuum between the liner and the socket.

Through the years, many socket structures have been developed for use with vacuum and non-vacuum systems alike. Many of these structures are represented in the patent literature. For example, U.S. Pat. No. 2,634,424 to O'Gorman discloses a double-walled socket of resiliently flexible material.

U.S. Pat. No. 5,007,937 to Fishman deals with a structure for enhanced retention of artificial limbs and method of fabrication in which an air impermeable sealing band of rubberized material is introduced between the patient's stump and the interior of a stump-receiving socket of an artificial limb, in one of two ways, depending on whether or not the patient wears a stump sock. If the patient wears a stump sock, the band of sealant material is impregnated into the stump sock. If the patient does not wear a stump sock, an impregnated sock is incorporated into the interior structure of the socket of the patient's prosthesis. The impregnated sock itself is fabricated by placing a conventional stump sock on a somewhat oversized form. An appropriate annular region on the sock is then masked off by means of tightly fitting plastic bags, and one of the plastic bags provides an enclosing outer sheath which encompasses the annular region and extends upwardly above the form. A rubberized material in liquid form is introduced through the top of the outer sheath and a vacuum is introduced below to draw the material into the annular region of the sock, so as to impregnate the same. The rubberized material penetrates the sock, is worked into an axially contoured shaped, and is then permitted to set. A stump-receiving socket for an artificial limb with an integral annular seal is fabricated by placing a stump sock with the seal on a cast of a patient's leg and then laminating the socket over the sock using conventional procedures for manufacturing stump-receiving sockets.

U.S. Pat. No. 5,108,456 to Coonan shows a prosthetic appliance for residual limb is disclosed comprising a prosthesis member having a cavity defined by side walls formed of a rigid molded material. A separate removable molded socket member formed of a flexible material is nested within cavity of the prosthesis member and is adapted to receive the residual limb. Several separate, independently inflatable bladders preferably attached to the exterior of the socket member, when inflated, act against the rigid side walls of the prosthesis member to resiliently force discrete portions of the socket member side walls inwardly to grip the residual limb. An inflation control means is provided in the form of at least one manually operable air pump and one or more manually operable air valves, one for each of said bladders, for selectively inflating the associated bladder separately and independently from the other bladders, so that the gripping pressure of the residual limb at each discrete portion of the socket member may be adjusted separately and independently by both the air pump and the air valves.

U.S. Pat. No. 5,156,629 to Shane is directed to a removable and adjustable prosthetic insert disposed between the stump of a limb and the socket of a prosthesis is comprised of a high strength, pliable polymeric material within which are formed a plurality of spaced air pockets, or voids, which are coupled together by a series of connecting channels, or passages. Using an air valve extending through the polymeric material and coupled to the closed air pocket/channel system, the air pockets may be inflated to fill the stump/socket interspace and provide a tight-fitting, air cushioned prosthetic socket attachment. The air inflatable prosthetic insert can accommodate changes in the condition of the stump and applies a uniform prosthetic attaching force thereto. Other embodiments also employ an inflatable air cushion and make use of spaced, solid spheres disposed between air passages arranged in a grid-like array; and pinched tubing with interconnecting air passages to form a series of inflatable nodules. An air cushion isolates the limb stump from the hard, rigid prosthesis socket for user comfort and provides a custom fit for improved control and maneuverability of the prosthetic device.

U.S. Pat. No. 5,139,523 to Paton discusses an apparatus for mounting a socket above the knee of an amputee, wherein the socket is arranged for mounting a prosthesis to a lower terminal end thereof. The sleeve includes an internal cage formed of rigid rods, including hook members imbedded within a semi-spherical sleeve support, with the cage encased in a polymeric covering. A vent is provided through the sleeve support for, venting interiorly of the socket. The socket may further include pneumatic chambers for enhanced comfort in support of the socket.

U.S. Pat. No. 5,888,231 to Sandvig describes a method of preparing a breathable, custom-molded liner for an artificial limb socket. The disclosed method includes the steps of providing a liner comprising an open-celled foam material impregnated with a curable resin, activating the curable resin, and deforming the foam material by positioning a residual limb on one of opposing surfaces of the liner, and positioning the artificial limb socket on a second opposing surface of the liner until curing is substantially complete to create and retain an impression of the residual limb in the foam material. A liner blank useful for preparing an artificial limb socket, comprising a foam material impregnated with a curable resin and sewn into the shape of a sock for an artificial limb, is also described.

U.S. Pat. No. 6,585,774 to Dean involves a dynamic variable geometry prosthetic fitting system with fluid-filled bladders and automatically regulating their volumes to provide a continuously secure fit. This system can vary volume continuously to accommodate natural variation in an amputee's residuum. It makes reliable suction retention of a prosthesis easier for the prosthetist to achieve while reducing the potential for tissue lesions. By maintaining a continuous, secure fit, the amputee's sense of confidence and willingness to use the prosthesis increases.

U.S. Pat. No. 6,926,742 to Caspers is directed to a hypobarically-controlled artificial limb for amputees. The Caspers device includes a single socket with a volume and shape to receive a substantial portion of the residual limb. A liner with a volume less than the residual limb is donned over the residual limb, with the liner tensioned into total contact relationship with the residual limb. A sealed cavity is formed between the socket and the liner. A vacuum source is connected to the socket cavity thereby drawing the residual limb and liner into firm and total contact with the socket. To compensate for some air leakage past the seal, there is a mechanism to maintain the vacuum in the cavity. A plate/socket attachment connects the vacuum source to the cavity.

Among the disadvantages of known systems are size, weight, and difficulty of use. There are many amputees that cannot use known systems because of size (particularly smaller adults and children), age of the patient, and length of the stump. For many patients, the time-consuming steps and cumbersome strap systems involved in using known prostheses cause the patients to eschew prostheses entirely. Further, known sockets are subject to unhygienic conditions, as they collect perspiration from the residual limb, and bacteria and other contaminants from the ambient air surrounding the prosthesis.

It can thus be seen from the foregoing that the need exists for a prosthetic socket that ameliorates the drawbacks of known devices, while remaining easy-to-use, lightweight, and hygienic.

These together with other objects of the invention, along with the various features of novelty which characterize the invention are pointed out with particularity in the claims annexed to and forming a part of this disclosure. For a better understanding of the invention, its operating advantages and the specific objects attained by its uses, reference should be had to the accompanying drawings and descriptive matter in which there is illustrated embodiments of the invention.

SUMMARY OF THE INVENTION

Generally, a socket assembly for use with a prosthetic device for hygienically and comfortably securing a prosthetic to a residual limb for attachment to a vacuum source is disclosed and claimed. The socket assembly comprises an outer shell capable of receiving a residual limb, a skin interface secured to at least a portion of the interior of the outer shell, and an air barb for communication between the interior and the exterior of the socket. In an aspect of an embodiment, the air barb may be connected to a vacuum source for evenly distributing the force through the skin interface. An aspect of an embodiment of the present device includes that the skin interface is vacuum-permeable.

An additional embodiment of the present device is provided in which the socket assembly further comprises a high-vacuum valve for communicating between the interior and the exterior of the socket assembly. In an embodiment of the device, a diffusion pillow is provided between the intake of the air barb and the interior of the socket assembly, where the diffusion pillow may comprise a synthetic fiber pillow. An aspect of an embodiment of the socket assembly provides that the outer shell is fabricated from plastic, such as thermoformable plastic, or from PETG.

In another aspect of an embodiment, the skin interface may be fabricated from a textile material, including a three-ply textile material such as a synthetic textile material, or from wool. Yet another aspect of an embodiment of the disclosed socket assembly is that it further comprises an annular vacuum seal secured to the interior of the socket assembly, one aspect of the annular vacuum seal being that it may be formed from urethane or silicone. In an additional embodiment, the skin interface extends over substantially all of the interior of the socket and further comprises an annular band extending over a portion of the interior of the socket.

These and other aspects of the invention may be understood more readily from the following description and the appended drawings.

BRIEF DESCRIPTION OF THE DRAWINGS

Embodiments of the invention are illustrated by way of example, and not by way of limitation, in the figures of the accompanying drawings and in which like reference numerals refer to similar elements and in which.

DETAILED DESCRIPTION OF PREFERRED EMBODIMENTS

In the following description, specific details are set forth in order to provide a thorough understanding of the invention. However, it will be apparent that the invention may be practiced without these specific details.

While this invention has been described in connection with the best mode presently contemplated by the inventor for carrying out his invention, the preferred embodiments described and shown are for purposes of illustration only, and are not to be construed as constituting any limitations of the invention. Modifications will be obvious to those skilled in the art, and all modifications that do not depart from the spirit of the invention are intended to be included within the scope of the appended claims. Those skilled in the art will appreciate that the conception upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention resides not in any one of these features per se, but rather in the particular combinations of some or all of them herein disclosed and claimed and it is distinguished from the prior art in these particular combinations of some or all of its structures for the functions specified.

Figure 1:
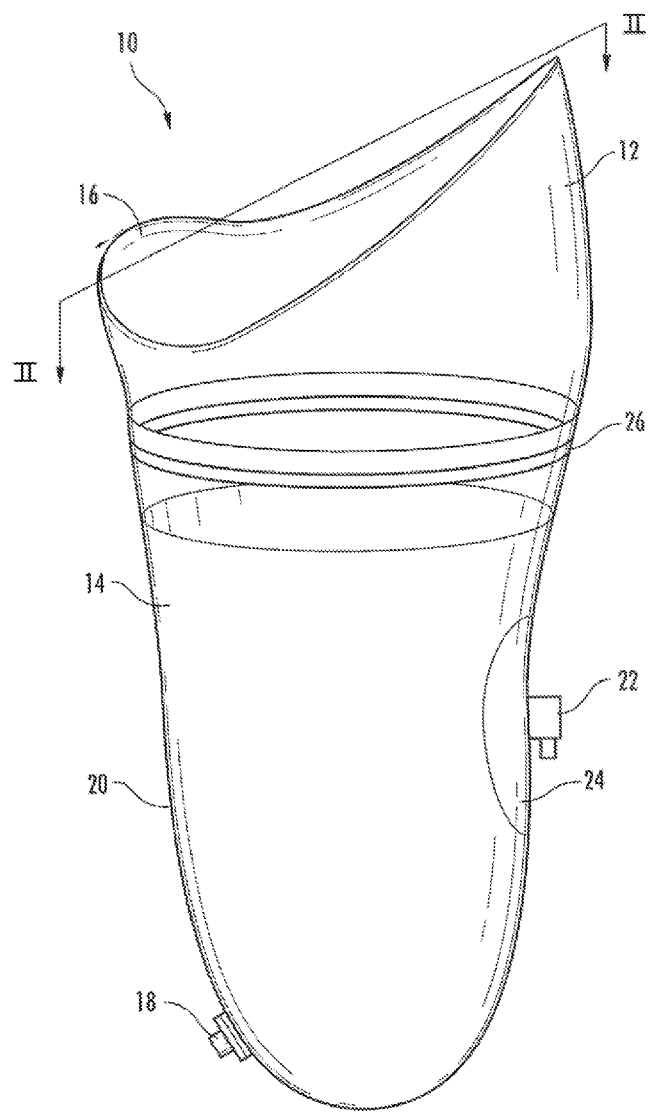
FIG. 1 is a perspective view of an embodiment of a socket assembly in accordance with the principles of the present invention.
Figure 2:
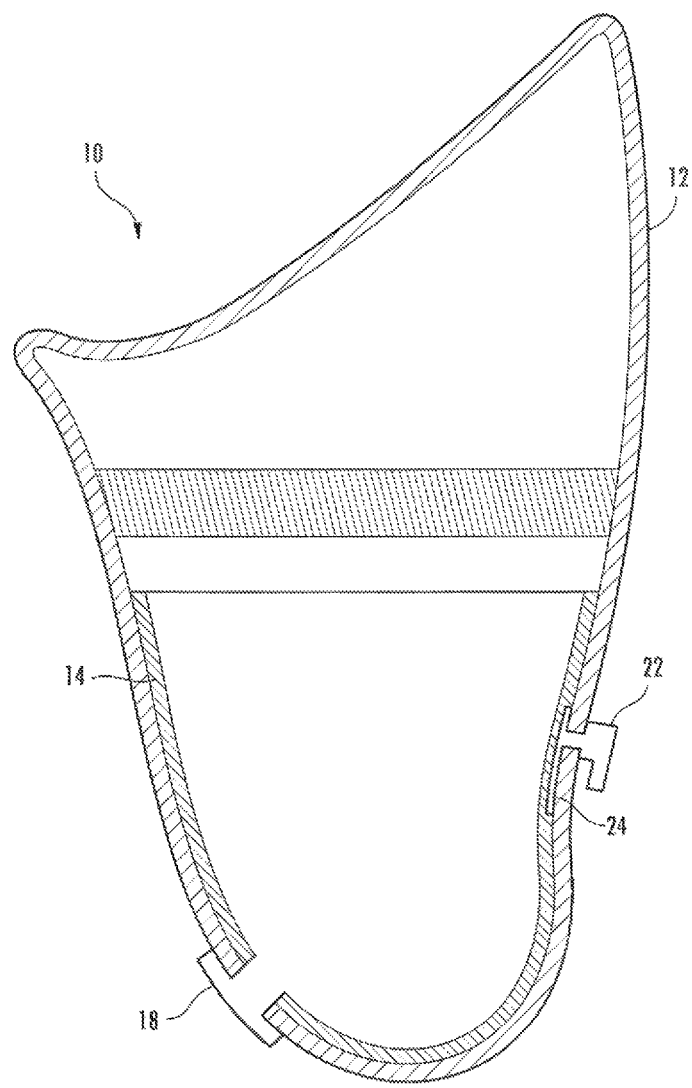
FIG. 2 is a sectional view taken generally along the plane parallel to line II-II of FIG. 1.

FIGS. 1 and 2 illustrate a socket assembly 10 in accordance with the principles of the present invention. The socket assembly 10 is suitable for use with any vacuum-assisted prosthetic system, but finds particular utility with the systems claimed and described in U.S. Ser. Nos. 11/640,150 and 12/286,474, the specifications of which are incorporated by reference herein. The socket assembly 10 includes an outer shell 12 fabricated from an airtight and relatively rigid material. The outer shell material must be capable of being thermoformed or vacuum-formed over a plaster mold cast from a residual limb to conform to the residual limb of the amputee to which the prosthesis is fitted. It is contemplated that a variety of thermoplastic materials will perform well. Examples of such materials are polyethylene terephthalate, including PETG manufactured by Kodak and available from a variety of sources, and NorthPlex, available from Endolite, Inc. of Centerville, Ohio. The formed shell can be further reinforced using carbon fiber, Kevlar mat or reinforcing material using an appropriate adhesive systems, such as being bonded to the socket using a peroxide-cured thermoset acrylic polymer or the like.

A skin interface 14 is secured to the interior 16 of the outer shell 12, for example, by adhesive or integral molding. The skin interface 14 advantageously covers a majority of the contact area between the socket assembly 10 and the residual limb of the user. The skin interface 14 is fabricated from a vacuum-permeable material, such as a three-ply textile material. It is contemplated that materials such as wool used in the three-ply sock available from DAWFLO, or a three-ply synthetic material such as that used in the KNIT-RITE A-PLUS sock are suitable.

A high-vacuum valve 18 is connected between the interior 16 of the socket assembly 10 and the exterior 20 of the socket assembly 10. One example of a suitable valve is available from ESP HV Valve of Newton, N.J. The high-vacuum valve 18 must be capable of holding sufficient vacuum to secure the socket assembly 10 to the residual limb of the user. The amputee pulls tissue into the socket assembly 10 via the high-vacuum valve 18 in a conventional manner. Using a donning sleeve, the user pulls the residual limb tissue into the socket and HV valve, then removes the donning sleeve via the HV valve.

An air barb 22 is secured to the outer shell 12, and includes an intake communicating with the interior 16 of the socket assembly 10 and an outlet communicating with the exterior 20 of the socket assembly 10. The air barb 22 is adapted and constructed for connection to a vacuum system as described in U.S. Ser. No. 11/640,150. The barb 22 is the portal through which air is evacuated from the interior of the socket assembly 10. One example of a suitable air barb is available from Clippard Tools of Cincinnati, Ohio. A diffusion pillow 24 is positioned between the intake of the air barb 22 and the skin interface 14. The diffusion pillow 24, which can be fabricated from a nonwoven fabric, for example, a Dacron felt material such as is available from PEL Inc. of Cleveland, Ohio, or any other suitable synthetic textile material. The diffusion pillow 24 is used to diffuse the source of vacuum, which may generate 24"HG, over a larger area to minimize the danger of tissue damage.

If desired, an additional vacuum seal 26 can be provided. The vacuum seal 26 is illustrated as an annular sealing member secured to the interior 16 of the socket assembly 10 at a location above the skin interface 14. The vacuum seal 26 is used as a supplemental vacuum seal for residual limbs with high volume fluctuations, and can be fabricated from a nonporous material such as urethane or silicone elastomer. One suitable seal member is an annular sleeve associated with suspension sleeves, as available from Otto Bock of Plymouth, Minn.

An alternative embodiment of a socket assembly 10 may provide for an annular band extending around a portion of the interior of the shell 16, as is known in the art. With many amputees, the end of the residual limb is unusually irregular in its topography. The irregular nature of such residual limbs renders it difficult to maintain vacuum in known socket assemblies. However, in the present invention, the vacuum is distributed through the skin interface. The annular band configuration of the skin interface 14 allows the contact area, and thus the vacuum distribution, to be limited to those areas of the residual limb having relatively regular and smooth surfaces, thus providing sufficient vacuum to retain the socket on the residual limb.

Selective placement of the skin interface allows the mapping of the socket to be placed only in those areas of the socket that will be in contact with portions of the residual limb capable of maintaining vacuum contact. Thus, areas with extensive scarring and/or irregular topography can be avoided, while areas with smoother tissue provide high-vacuum areas. For example, in a stance (standing) position, the contact portion of the residual limb is under high vacuum, while the irregular portion is under no vacuum. In a step (swing) action, the irregular portions of the residual limb will experience at most 2.5" Hg to 3" Hg, far less than will cause tissue damage.

The socket assembly 10 of the present invention provides many advantages over known systems. For example, it is contemplated that most applications of the socket assembly of the present invention will weigh on the order of 6 ounces to 2 pounds, and require 1 minute or less to put on. The present invention eliminates the need for the use of gels or lubricants to prepare the limb. Significantly, the direct contact of the skin interface with the limb allows the socket assembly of the present invention to vaporize perspiration, thus enhancing the comfort level and overall hygiene of the user. The reduced weight also simplifies the tasks required by systems that may be associated with the prosthetic device.

With respect to the above description, it is to be realized that the optimum dimensional relationships for the parts of the invention, including variations in size, materials, shape, form, function and manner of operation, assembly and use, and all equivalent relationships to those illustrated in the drawings and described in the specification, that would be deemed readily apparent and obvious to one skilled in the art, are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A socket assembly for use with a prosthetic device, the socket assembly capable of receiving at least a portion of a residual limb on which the prosthetic device is attached, the socket assembly comprising:
   an outer shell configured to fit onto the residual limb, the shell having an interior surface and an exterior surface;
   a vacuum-permeable skin interface attached to the interior surface of the outer shell only in selected areas where the vacuum-permeable skin-interface contacts skin of the residual limb capable of maintaining vacuum contact; and
   an air barb having an intake and an outlet, the air barb communicating between an interior of the socket assembly and an exterior of the socket assembly, and being configured to attach to a vacuum source;
   whereby, when the residual limb is positioned in the socket assembly and the air barb is connected to a vacuum source, a vacuum force exerted by the source is evenly distributed through the vacuum-permeable skin interface to the selected areas contacting skin of the residual limb.

2. A socket assembly in accordance with claim 1, further comprising a high-vacuum valve communicating between the interior of the socket assembly and the exterior of the socket assembly.

3. A socket assembly in accordance with claim 1, further comprising a diffusion pillow secured between the intake of the barb and the interior of the socket assembly.

4. A socket assembly in accordance with claim 3, wherein the diffusion pillow comprises a synthetic fiber pillow.

5. A socket assembly in accordance with claim 1, wherein the outer shell is fabricated from plastic.

6. A socket assembly in accordance with claim 5, wherein the outer shell is fabricated from a thermoformable plastic.

7. A socket assembly in accordance with claim 6, wherein the outer shell is fabricated from PETG.

8. A socket assembly in accordance with claim 1, wherein the skin interface is fabricated from a textile material.

9. A socket assembly in accordance with claim 8, wherein the skin interface is fabricated from a three-ply textile material.

10. A socket assembly in accordance with claim 9, wherein the skin interface is fabricated from a synthetic textile material.

11. A socket assembly in accordance with claim 9, wherein the skin interface is fabricated from wool.

12. A socket assembly in accordance with claim 1, further comprising an annular vacuum seal secured to the interior of the socket assembly at a location outward of the skin interface.

13. A socket assembly in accordance with claim 12, wherein the annular vacuum seal is fabricated from urethane.

14. A socket assembly in accordance with claim 12, wherein the annular vacuum seal is fabricated from silicone.

15. A socket assembly in accordance with claim 1, wherein the skin interface extends over substantially the entire interior surface of the outer shell.

16. A socket assembly in accordance with claim 1, wherein the skin interface comprises an annular band extending over a portion of the interior of the socket assembly.

17. A socket assembly for use with a prosthetic device, the socket assembly capable of receiving a residual limb on which the prosthetic device is attached, the socket assembly comprising:
   an outer shell configured to fit onto the residual limb, the shell having an interior surface and an exterior surface;
   a vacuum-permeable skin interface attached to the interior surface of the outer shell only in selected areas where the vacuum-permeable skin interface will contact skin of the residual limb capable of maintaining vacuum contact;
   a high-vacuum valve communicating between an interior of the socket assembly and an exterior of the socket assembly;
   an air barb having an intake communicating with the interior of the socket assembly and an outlet communicating with the exterior of the socket assembly, the air barb being configured to attach to a vacuum source; and
   an annular vacuum seal secured to the interior of the socket assembly at a location above the skin interface;
   whereby, when the residual limb is positioned in the socket assembly and the air barb is connected to a vacuum source, a vacuum force exerted by the source is evenly distributed through the skin interface to the selected areas contacting skin of the residual limb.

* * * * *